United States Patent [19]
Porter

[11] Patent Number: 6,153,213
[45] Date of Patent: Nov. 28, 2000

[54] MEANS FOR SUPPLYING A BENEFICIAL SUBSTANCE TO AN ANIMAL

[76] Inventor: William Leslie Porter, Animax Ltd., Shepherds Grove West, Stanton, Bury St. Edmunds, Suffolk IP31 2AR, United Kingdom

[21] Appl. No.: 09/259,400

[22] Filed: Feb. 26, 1999

[30] Foreign Application Priority Data

Mar. 18, 1998 [GB] United Kingdom .................... 9805623
Mar. 18, 1998 [GB] United Kingdom .................... 9805625
Mar. 18, 1998 [GB] United Kingdom .................... 9805629

[51] Int. Cl.$^7$ ...................................................... A61K 9/00
[52] U.S. Cl. .......................... 424/438; 424/453; 424/454; 604/892.1
[58] Field of Search ............................ 424/438, 424–426, 424/430–434, 436, 442, 453, 454, 458–462, 408; 604/890.1, 891.1, 892.1

[56] References Cited

U.S. PATENT DOCUMENTS 4,595,583 6/1986 Eckenhoff et al. .
5,180,591 1/1993 Magruder et al. ...................... 424/423

FOREIGN PATENT DOCUMENTS 2122086 1/1984 United Kingdom .

Primary Examiner—Neil S. Levy
Attorney, Agent, or Firm—Edwin D. Schindler

[57] ABSTRACT

Means for delivering a beneficial substance such as vitamin E to an animal, employing a pump means in the form of a device (10, 110 or 210) containing a material such as a silicate gel which swells by absorption of waer, for example from the digester in the case of a bolus, to apply pressure to an elastic container for the beneficial substance, whereby to cause the beneficial substance to be expelled through an exit orifice.

13 Claims, 4 Drawing Sheets

MEANS FOR SUPPLYING A BENEFICIAL SUBSTANCE TO AN ANIMAL

FIELD OF THE INVENTION

This invention relates generally to means for supplying a beneficial substance to an animal and more specifically to a device for external use to supply the beneficial substance to the animal and to a bolus for oral administration to release the beneficial substance internally.

PRIOR ART

Known from the prior art are devicees such as that disclosed in U.S. Pat. No. 4,844,984 utilising osmosis for the purpose of delivering a beneficial substance to an animal.

BRIEF SUMMARY OF THE INVENTION

According to one aspect of the invention there is provided a device for supplying a beneficial substance to an animal, comprising a container divided by a water-permeable filter into a first section for containing water and a second section, the second section in use of the device having an exit orifice and being divided in its interior by an elastic component into a first compartment containing a material which swells by absorption of water and a second compartment containing the beneficial substance, the first compartment being in communication with the filter and the second compartment being in communication with the exit orifice.

The above-defined device is intended to be used for supplying the beneficial substance to an animal over a relatively prolonged period of time of at least three months, preferably at least six months and, desirably, up to a year or more, for which purpose it may be coupled to a mouthpiece fitting or fistular device or hook-ended dosing pipe to enable oral administration, but alternatively may be coupled to a licking pad, or even apply the beneficial substance directly to the animal's coat, to enable the beneficial substance to be supplied by absorption through the skin. For any such purpose, the first section is supplied with water, possibly by coupling to a water reservoir but alternatively by injection from a syringe. The water slowly passes through the filter into the swellable material, causing the first compartment gradually to expand due to deformation of the elastic partitioning component, with resulting compression of the second compartment, whereby the beneficial substance is slowly forced out of the exit orifice to be supplied to the animal. The exit orifice may be preformed and initially sealed, to be opened when the device is to be used, or it may be formed, e.g. by piercing the wall of the second section, when the device is to be used.

A variety of water-absorbent gels and granules are readily available for use as the swellable material. Examples are silicates, polyacrylates and polyacrylamides.

The elastic component is preferably envelope shaped. Preferably the interior of this envelope constitutes the first compartment containing the swellable material.

This swellable material in the first compartment in swelling due to absorption of water, may then compress the second compartment containing the beneficial substance, which is thus expelled through the exit orifice.

The container itself, especially the first section, may also be made of an elastic material, for example taking the form of a waisted, elongate balloon having a water-receiving slightly bulbous section at one end separated by the waist, whereat the filter is located, from a slightly bulbous section at the other end which contains the elastic partitioning component, the swellable material and the beneficial substance. The first mentioned section is thereby able to swell to a limited extent to accommodate a greater quantity of water, whilst the second section may expand to a limited extent to assist linearisation with time of the delivery of the beneficial substance. A tie or fastener around the waist can be employed to fix the location of the filter. It is, however, equally feasible to employ a rigid container, in which case an air bleed is desirable for the water-receiving first section.

According to a second aspect of the invention, there is provided a bolus for supplying a beneficial substance to a ruminant animal, comprising an open-ended elongate container closed by a water-permeable filter at one end and at the other end in use of the device having an exit orifice, the interior of the container being compartmented by means of an elastic component into a first compartment containing a material which swells by absorption of water and a second compartment containing the beneficial substance, the first compartment being in communication with the filter and the second compartment being in communication with the exit orifice. Again, the exit orifice may be preformed and initially sealed, to be opened when the bolus is to be used, or it may be formed, e.g. by piercing the wall of the container, when the bolus is to be used.

This bolus is thus substantially the same as the device previously defined, except for the omission of the water-containing first section. In use, after oral administration, the bolus resides in the digestive tract (rumen or reticulum) and water is absorbed through the filter from the stomach content.

The further features of the previously defined device are also generally applicable to the bolus, having due regard to the fact that the water-containing first section is absent. However, in order to assist prolonged retention in the digestive tract, a ballast material, such as a non-toxic metal or metal component is preferably incorporated. This ballast material may be incorporated into the first compartment, for example in a region surrounding the exit mouth, or may be incorporated externally to the container, but is preferably incorporated with the swellable material.

According to another aspect of the invention there is provided a bolus for a ruminant animal comprising two or more bodies linked by one or more connecting elements, at least one of the bodies being a hollow body having an exit orifice from which the beneficial substance can be forced out under pressure when the bolus is resident in the digestive tract of the animal following oral administration, and pump means within the body whereby the beneficial substance is subject to the pressure necessary to cause it to be delivered through the exit orifice, the pump means being a material which swells on absorption of water.

A variety of gels and granules for constituting the water absorption material are readily available, including silicate, polyacrylate and polyacrylamide materials. When the bolus is resident in the digestive tract (rumen or reticulum), this swellable material may receive water from the digestive tract through a filter forming at least a part of the wall of the hollow bolus. The pressure generated by the swelling material may then be applied to the beneficial substance through a small piston or an elastic partitioning element separating the beneficial substance from the silicate gel or other swellable material.

A preferred bolus has two or more similarly-operating bodies interconnected by the connecting element, which is preferably flexible and may be constituted by a plastics cord or tape or the like. Either one or each of the bodies may also incorporate an amount of ballast material, such as a non-toxic metal or metal compound.

Preferably, in order to facilitate oral administration of the bolus, a means is provided for holding the bodies in a formation facilitating administration in this way. This holding means is desirably made of a material which dissolves or disintegrates or expands in the digestive tract to free the interconnected bodies for long life retention.

A preferred holding means is a tube, for example of cardboard or dissolvable paper, in which the two or more bodies are assembled in close formation, typically end to end.

Beneficial substances which can be delivered to the animal in substantial amounts, by means of the bolus, include nutrients such as trace elements and vitamins such as vitamin E, and medicaments. Two or more such beneficial substances may be delivered simultaneously. Such substances include zinc or other compounds for controlling fungal, bacterial, protozoal, parasitic (endo- or ecto-) conditions, other vitamins, lipids and the like.

In the modification of the present invention, in the bolus as defined above, the closed end of each body is made of a piercable material whereby, in conjunction with a piercing implement, the wall of the container or body can be pierced to create an exit orifice for the beneficial substance immediately prior to oral administration of the bolus to the animal.

According to still another aspect of the invention, there is provided a system for delivering a beneficial substance to an animal over a prolonged period (at least three months, preferably six months, and desirably up to a year or more), comprising a source of the beneficial substance, application means whereby the beneficial substance can be externally administered to the animal, and pump means associated with the source whereby the beneficial substance is fed from the source to the application means, wherein the pump means comprises a device containing a material which swells by absorption of water, thereby to apply pressure to a compressible container for the beneficial substance, causing the substance to be fed to the application means.

The compressible container may be constituted by a flexible envelope or a cylinder/piston device, for example.

Generally, but not essentially, the source will also be carried by the animal externally, typically remotely from the application means, to which it will be connected by suitable tubing.

The application means may take a number of forms. For oral administration, a hollow bit with an orifice for delivery of the beneficial substance may be employed, or a hook-ended dosing pipe such as that shown in U.K. Patent No. 1 554 212, or a shaped mouthpiece fitting, or a fistular device such that the beneficial substance is delivered through the animal's cheek. However, certain beneficial substances may alternatively be administered by absorption through the skin, by controlled delivery of the beneficial substance to a licking pad (a pad coated with a material attractive to licking by the animal) applied to the skin or possibly by direct delivery to the animals skin or coat, all as hitherto explained.

BRIEF DESCRIPTION OF THE DRAWINGS

The invention is further described with reference to the accompanying drawings, in which.

DESCRIPTION OF EMBODIMENTS

Figure 1:
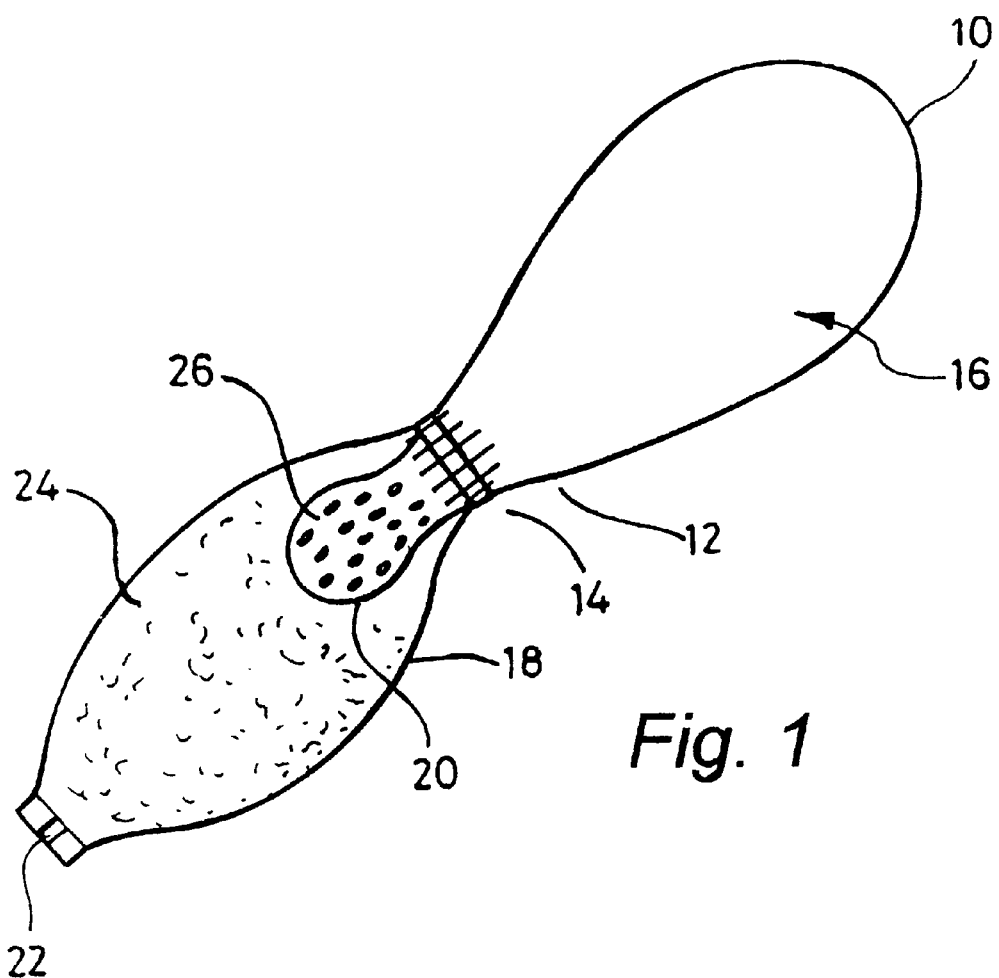
FIG. 1 shows a device for use in external delivery of a beneficial substance to an animal.

Referring to FIG. 1, the illustrated device comprises an elongate waisted balloon-shaped container 10, for example made of rubber substitute which is only slightly elastic, but which could alternatively be made of a wholly non-elastic material.

The container 10 is divided into two sections by a water-permeable filter 12, which may be held in place by an external compression band 14.

The first section 16 of the container is intended to hold water, for example received from a reservoir but alternatively injected by means of a syringe.

The second section 18 is divided into two compartments by an envelope-shaped partitioning component 20, for example made of rubber or other impervious elastic material. An open end of the section 18 communicates with an exit orifice 22, initially sealed but opened when the device is to be used.

The compartment 26 substantially surrounded by the compartment 24 defined by the envelope 20 contains a gel or granules, of which many kinds are readily available, which swells substantially on absorption of water. The compartment 24 contains the beneficial substance to be delivered to the animal. This substance may be a nutrient such as a vitamin, for example vitamin E, or it may be a medicament, or it may be a mixture of two or more beneficial substances (trace elements, bacteriocides, fungicides, parasiticides, anthelmintics, coccicides, antiprotozoals, growth promoters, anti-bloat substances, or other nutrients and/or medicaments).

In use, when the section 16 is supplied with water, this gradually passes through the filter 12 into the compartment 26, whereby to be absorbed by the swellable material, causing expansion thereof. The elastic envelope 20 is thereby expanded, or balloons, under the generated internal pressure, causing the beneficial substance(s) in the compartment 24 to be forced out through the now unsealed exit orifice 22. The device is not exhausted until the envelope 20 balloons substantially fills the section 18.

From the exit orifice 22, the beneficial substance may be delivered to the animal via a suitable mouthpiece, or via a licking pad on the skin (a pad coated with a material attractive to licking by the animal), or possibly even by direct application to the animal's coat. Obviously some beneficial substances cannot be delivered by absorption through the skin, so the method of final delivery is partly dependent on the nature of the beneficial substance(s).

Figure 2:
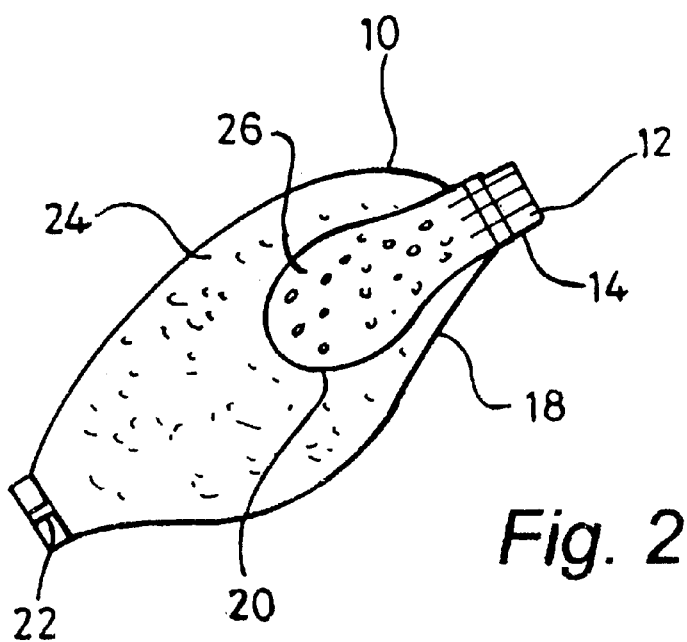
FIG. 2 shows a modification in the form of a bolus for internally delivering the beneficial substance to a ruminant animal.

The device shown in FIG. 2 is a bolus, generally similar to the device described with reference to FIG. 1 but having the water-containing section omitted. Similar references are used for similar parts.

This bolus is intended for oral administration to a ruminant animal, where it is intended to reside in the rumen or reticulum so that water is absorbed through the filter from the rumeno-reticulum contents.

As the device is intended to be resident in the rumen or reticulum for a relatively prolonged period, for example at least three months, preferably six months and most desirably a year, ballast material 28, for example in the form of a non-toxic metal or metal component, is incorporated, for example in an annular region surrounding the mouth-end region of the envelope 20, but most preferably along with the swellable material in the compartment 26.

In a modification, applicable to the device of FIG. 1 or the bolus of FIG. 2, the container 10, instead of being preformed with the exit orifice 22, is made of a piercable material, e.g. rubber substitute as previously mentioned, which can be pierced by a piercing implement, whereby to form the required exit orifice prior to administrative use.

Figure 3:
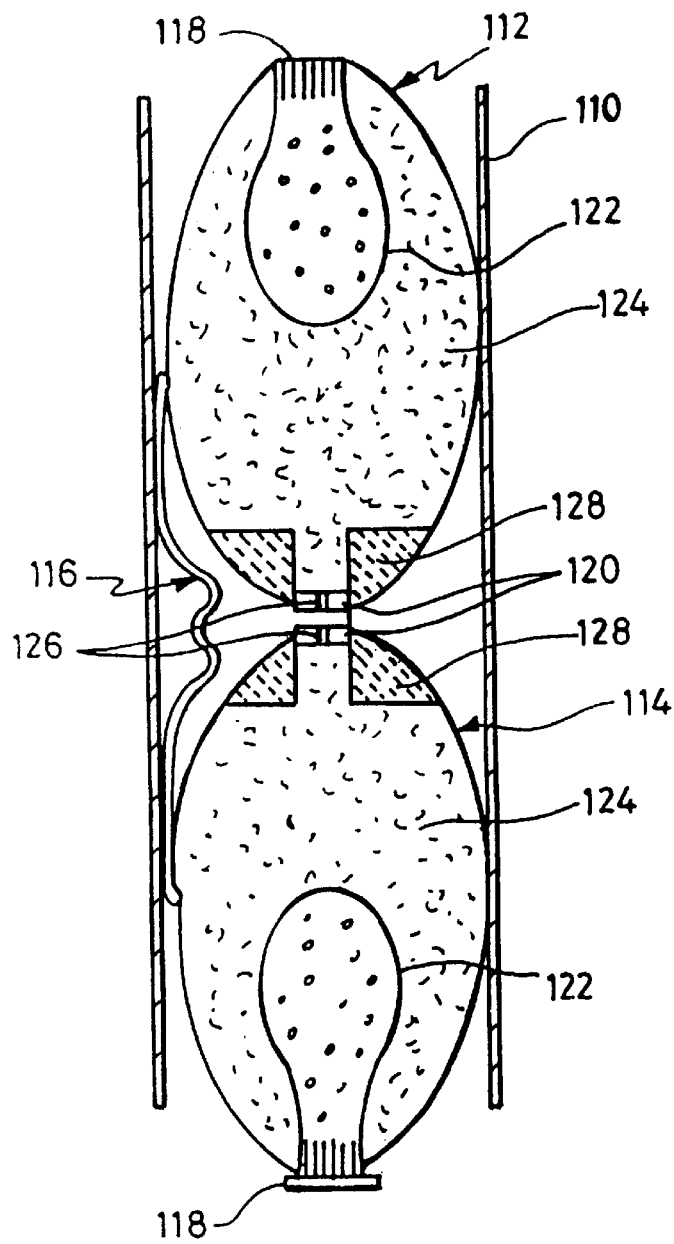
FIG. 3 shows a preferred double bolus diagrammatically.

The double bolus shown in FIG. 3 comprises a cardboard tube 110 in which two bolus bodies 112, 114 are assembled, interconnected by a flexible cord 160.

The two bolus bodies 112, 114 are hollow, being moulded for example of a rubber substitute of minimal elasticity, the interconnecting cord 116 being integrally formed therewith to join two intermediate points, preferably central points, in the lengths of the two bodies, whereby if one body enters the oesophagus, the other body is drawn transversely against the entrance to the oesophagus, thus preventing regurgitation.

Each bolus body comprises an elongate container closed at one end by a filter element 118 and at the other end by a plug 120. The filter 118 opens into the mouth of an elastic envelope 122 in which the swellable material such as silicate granules is contained. The envelope 122 is at least partly surrounded by a space 124 in which the beneficial substance is contained. In use the swellable material receives water from the rumeno-reticulum via the filter 118.

The plug 120 contains an initially sealed exit orifice 126 opened when the bolus is to be used by oral administration to the ruminant animal. In the digestive tract, the tube 110 disintegrates, whereby the bodies 112, 114 are free to drift apart, giving the inherent capability to the bolus for long life retention in the digestive tract. The incorporation of ballast material in each body, as indicated at 128 for example, but possibly mixed with the swellable material, also assists retention in the digestive tract.

When the bolus is resident in the digestive tract (rumen or reticulum), each body takes in water from the animal's stomach through the respective filter elements 18, whereby the silicate granules or like material is caused to swell, causing expressive pressure to be applied to the elastic envelope 120, thus forcing the beneficial substance out of the respective exit orifices 126.

The two bolus bodies 112, 114 are able to deliver to the animal substantial quantities of a beneficial substance, for example a vitamin such as vitamin E, over a period of time of at least three months and preferably up to at least a year.

Figure 4:
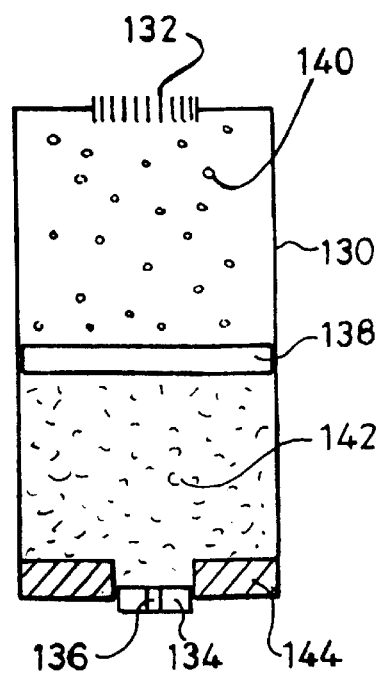
FIG. 4 shows a modification.

FIG. 4 shows an alternative bolus body for use instead of either one or more usually each of the above-described bolus bodies 112, 114.

In the modification, a more rigid container 130, for example of plastics material, is employed. The container 130 is again closed at one end by a filter element 132 and at the other end by a plug 134 having an exit orifice 136. However, instead of an elastic envelope, a sliding piston 138 separates the silicate or other swellable material 140 from the beneficial substance 142. Ballast 144 may also be incorporated, for example as shown, but alternatively in the form of a metal tube incorporated as part of the bolus.

In use, the piston 138 is generally driven towards the exit end of the bolus by the pressure generated by swelling of the silicate material when the latter absorbs water from the animal's stomach via the filter element 118, the movement of the piston causing the beneficial substance to be delivered through the exit orifice 126.

Again, two such bolus bodies are interconnected by a flexible cord joining central or near central points in the lengths of the bolus bodies, and for administration purposes the two bolus bodies are initially contained in a cardboard or other dissolving or disintegrating tube. As with the bolus of FIG. 3, a disintegrating or dissolving or expanding tape could be used to hold the bodies together initially, instead of the cardboard or paper tube.

Figure 5:
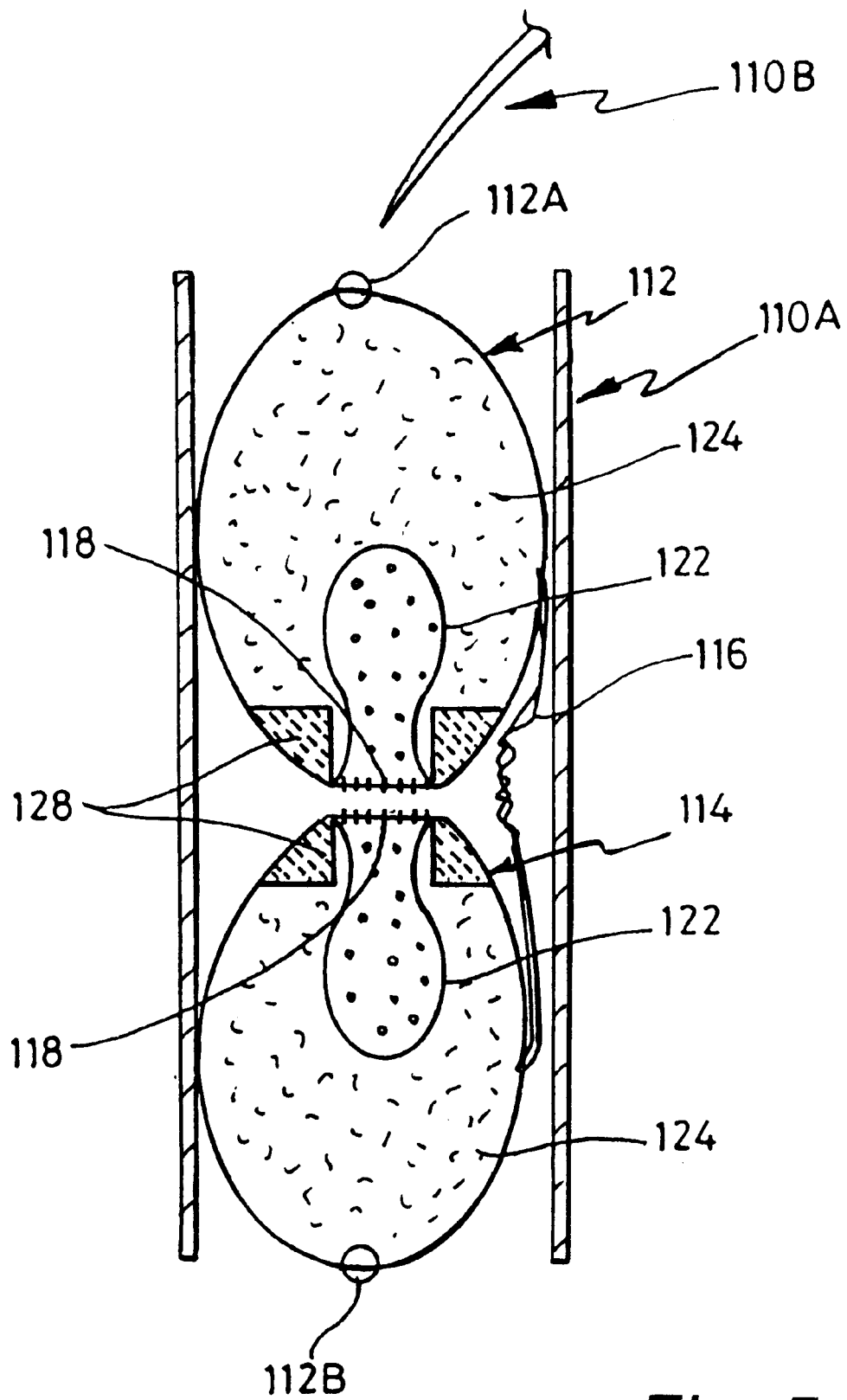
FIG. 5 shows a further modification.

A further modification is shown in FIG. 5, wherein the bolus 110A, substantially as described with reference to FIG. 3 except for the exit orifice 126, is shown in conjunction with a thin, narrow blade or needle device 110B, to be used for piercing the walls of the bodies 112, 114 at say the points 112A, 112B, immediately prior to administration of the bolus to a ruminant animal. The same reference numerals as used in FIG. 3 apply to FIG. 5 for corresponding parts, from which it will be understood that in FIG. 5 the bodies 112, 114 are packed into the tube in reversed orientations.

It is possible to produce a bolus having three or more bolus bodies if desired.

Figure 6:
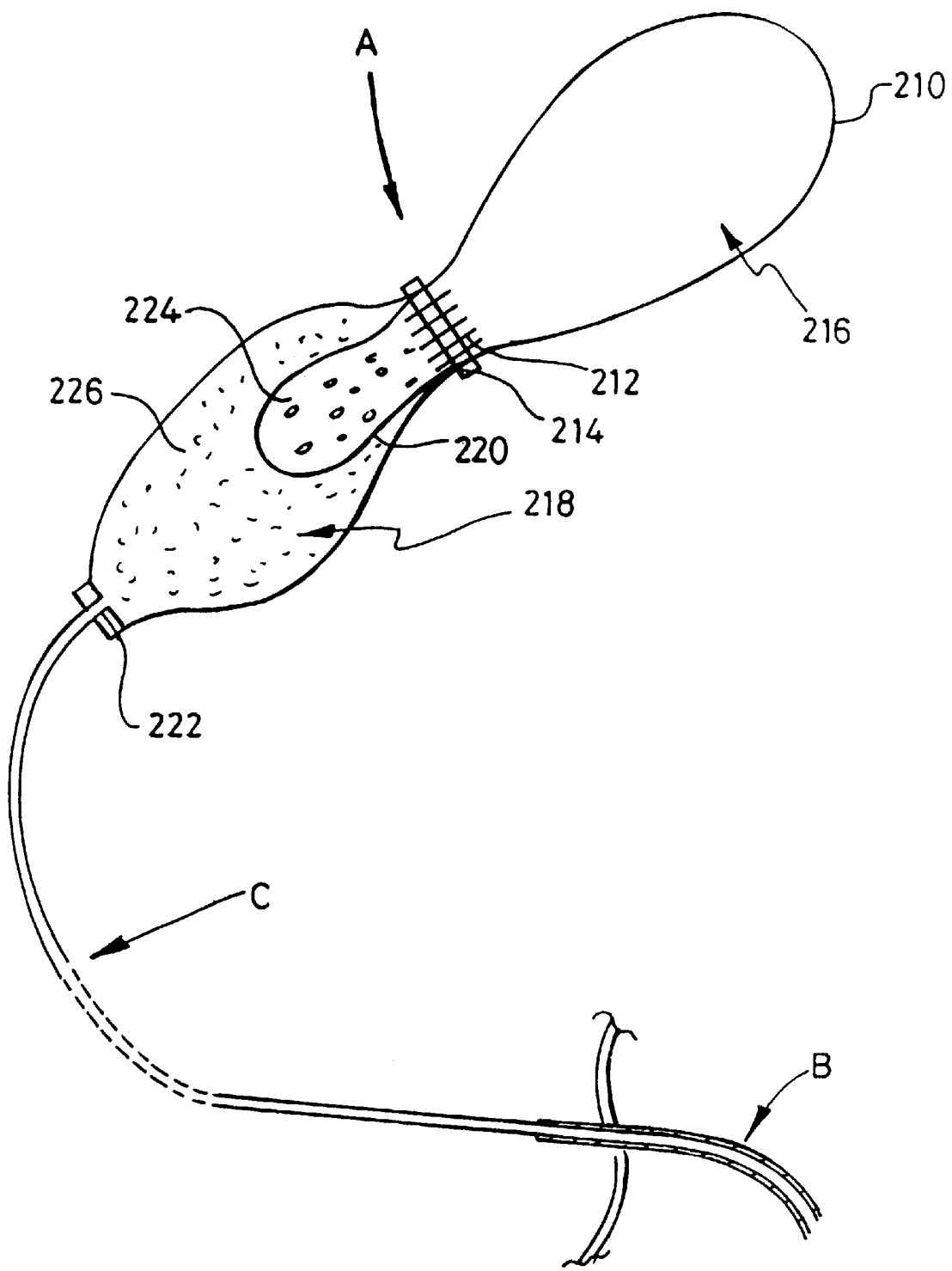
FIG. 6 shows a system for administering a beneficial substance to an animal.

The system shown in FIG. 6 is intended for delivering a beneficial substance from a source thereof to an animal over a prolonged period of time. The substance, generally in liquid form, may comprise a mineral, a vitamin such as vitamin E, or a medicament or any substance which has a beneficial nutritional or medicinal effect or a combination of any such substances, including trace elements, zinc or other compounds for controlling fungal, bacterial, protozoal or parasitic conditions, other vitamins, lipids and the like.

The system comprises a device A consisting of a source of the beneficial substance in combination with a pump, later described, a hooked mouthpiece B via which the substance is orally administered to the animal, and a connecting tube C.

In use, the device A is fixed to the animal, as by a strap or by tape, as for example a neckband, and the mouthpiece B is hooked into the side of the animal's mouth and secured irremovably in position, as by means of a halter. Such a mouthpiece does not prevent the animal from grazing or otherwise eating and drinking normally. The device A is then put into operation to deliver via the tube a steady supply of the beneficial substance to the mouthpiece over a prolonged period of up to several months.

The device A comprises an elongate waisted balloon-shaped container 210, for example made of rubber substitute which is preferably only slightly elastic, but which could alternatively be made of a wholly non-elastic material.

The container 210 is divided into two sections by a water-permeable filter 212, which may be held in place by an external compression band 214.

The first section 216 of the container is intended to hold water, for example received from a reservoir but alternatively injected by means of a syringe.

The second section 218 is divided into two compartments by an envelope-shaped partitioning component 220, for example made of rubber or other impervious elastic material. An open end of the envelope 220 communicates with the filter 212. At the other end of the section 218 is an exit orifice 222, initially sealed but opened when the device is to be used to feed the beneficial substance through the tube C to the mouthpiece B.

The compartment 224 defined by the envelope 220 contains a gel or granules, such as silicates, polyacrylates and polyacrylamides, but of which many kinds are readily available, which swells substantially on absorption of water.

The compartment 226 substantially surrounding the compartment 224 contains the beneficial substance to be delivered to the animal. This substance may be a nutrient such as a vitamin, for example vitamin E, or it may be a medicament, or it may be a mixture of two or more beneficial substances, examples of which have been previously mentioned.

In use, when the section 216 is supplied with water, this gradually passes through the filter 212 into the compartment 224, whereby to be absorbed by the swellable material, causing expansion thereof. The elastic envelope 220 is thereby expanded under the generated internal pressure, causing the beneficial substance(s) to be forced out through the now unsealed exit orifice 222, into and through the tube C to the mouthpiece B. The device is exhausted only when the envelope 20 substantially fills the section 18.

Other kinds of mouthpiece may be used, and the beneficial substance may alternatively be administered to the animal via a licking pad, or possibly even by direct application to the animal's coat. Obviously some beneficial substances cannot be administered by absorption through the skin, so the method of final delivery is partly dependent on the nature of the beneficial substance(s).

In the case of a stabled animal, the source of the beneficial substance, together with the pump, may be mounted to the structure of the animal's stall.

What is claimed is:

1. A bolus for supplying a beneficial substance to a ruminant animal, comprising:
    an elongate outer container, in use, having an exit orifice at its first end;
    a ballooning component of elastic material within said elongate outer container, said balloon-shaped component having a mouth closing a second end of said elongate outer container;
    a material capable of swelling by absorption of water filling said ballooning component;
    a filter closing the mouth of said ballooning component, said filter being permeable to water and impermeable to said material filling said ballooning component; and,
    a beneficial substance filling said elongate outer container outside said ballooning component, so that, when in use, said ballooning component expands by absorption of water from an animal rumen through said filter into said swellable material, thereby expanding said ballooning component and expelling said beneficial substance through said exit orifice of said elongate outer container until said ballooning component substantially fills said elongate outer container.

2. The bolus for supplying a beneficial substance to a ruminant animal according to claim 1, wherein said swellable material comprises a silicate.

3. The bolus for supplying a beneficial substance to a ruminant animal according to claim 1, wherein said swellable material includes a polyacrylate.

4. The bolus for supplying a beneficial substance to a ruminant animal according to claim 1, wherein said swellable material includes a polyacrylamide.

5. The bolus for supplying a beneficial substance to a ruminant animal according to claim 1, wherein said beneficial substance includes Vitamin E.

6. The bolus for supplying a beneficial substance to a ruminant animal according to claim 1, further comprising a ballast material in said elongate outer container for assisting retention in the digestive tract of the ruminant animal.

7. A bolus for supplying a beneficial substance to a ruminant animal, comprising:
    two or more units, each of said units including:
        an elongate outer container, in use, having an exit orifice at its first end;
        a ballooning component of elastic material within said elongate outer container, said ballooning component having a mouth closing a second end of said elongate outer container;
        a material capable of swelling by absorption of water filling said ballooning component;
        a filter closing the mouth of said balloon-shaped component, said filter being permeable to water and impermeable to said material filling said ballooning component; and,
        a beneficial substance filling said elongate outer container outside said ballooning component, so that, when in use, said ballooning component expands by absorption of water from an animal rumen through said filter into said swellable material, thereby expanding said ballooning component and expelling said beneficial substance through said exit orifice of said elongate outer container until said ballooning component substantially fills said elongate outer container; and,
    one or more connecting elements for connecting said units to one another.

8. The bolus for supplying a beneficial substance to a ruminant animal according to claim 7, wherein said one or more units are connected together in a tube for facilitating oral administration, said tube being of a material which dissolves, disintegrates or expands in the digestive tract of the ruminant animal for freeing the interconnected units for long-life retention in the digestive tract.

9. The bolus for supplying a beneficial substance to a ruminant animal according to claim 7, wherein said swellable material comprises a silicate.

10. The bolus for supplying a beneficial substance to a ruminant animal according to claim 7, wherein said swellable material includes a polyacrylate.

11. The bolus for supplying a beneficial substance to a ruminant animal according to claim 7, wherein said swellable material includes a polyacrylamide.

12. The bolus for supplying a beneficial substance to a ruminant animal according to claim 7, wherein said beneficial substance includes Vitamin E.

13. The bolus for supplying a beneficial substance to a ruminant animal according to claim 7, further comprising a ballast material in said elongate outer container for assisting retention in the digestive tract of the ruminant animal.

* * * * *